US009333502B1

(12) United States Patent
Ayliffe (10) Patent No.: US 9,333,502 B1
(45) Date of Patent: May 10, 2016

(54) SAMPLE-ACQUIRING MICROFLUIDIC TESTER (75) Inventor: Harold E. Ayliffe, Hailey, ID (US)

(73) Assignee: E. I. SPECTRA, LLC, Ketchum, ID (US)

( * ) Notice: Subject to any disclaimer, the term of this patent is extended or adjusted under 35 U.S.C. 154(b) by 736 days.

(21) Appl. No.: 13/615,252

(22) Filed: Sep. 13, 2012

(51) Int. Cl.
B01L 3/00 (2006.01)
G01N 35/10 (2006.01)

(52) U.S. Cl.
CPC ..... *B01L 3/50273* (2013.01); *B01L 2300/0887* (2013.01); *G01N 35/1016* (2013.01)

(58) Field of Classification Search
CPC .................. B01L 2300/0645; B01L 2200/027; B01L 2300/0874; B01L 3/502761; B01L 3/502715; B01L 2300/0816; B01L 2400/0481; B01L 3/5027; B01L 3/50273; B01L 2300/0887; G01N 15/1056; G01N 15/12; G01N 2015/1062; G01N 2015/1037; G01N 35/1016
See application file for complete search history.

(56) References Cited

U.S. PATENT DOCUMENTS

| 4,592,227 | A | * | 6/1986 | Poncept | 73/61.65 |
|---|---|---|---|---|---|
| 6,816,257 | B2 | | 11/2004 | Goix | |
| 7,417,418 | B1 | | 8/2008 | Ayliffe | |
| 7,515,268 | B1 | | 4/2009 | Ayliffe et al. | |
| 7,520,164 | B1 | | 4/2009 | Ayliffe | |
| 7,579,823 | B1 | | 8/2009 | Ayliffe | |
| 7,835,000 | B2 | | 11/2010 | Graves et al. | |
| 8,015,887 | B2 | | 9/2011 | Ayliffe et al. | |
| 8,072,603 | B2 | | 12/2011 | Ayliffe et al. | |
| 8,153,949 | B2 | | 4/2012 | Kiesel et al. | |
| 8,171,778 | B2 | | 5/2012 | Ayliffe | |
| 8,182,635 | B2 | | 5/2012 | Ayliffe et al. | |
| 8,188,438 | B2 | | 5/2012 | Li | |
| 8,743,352 | B2 | | 6/2014 | Gong | |
| 2011/0162439 | A1 | | 7/2011 | Ayliffe | |
| 2011/0189650 | A1 | | 8/2011 | Ayliffe et al. | |
| 2011/0189714 | A1 | | 8/2011 | Ayliffe et al. | |

FOREIGN PATENT DOCUMENTS

| WO | WO 2009/045343 | 4/2009 |
|---|---|---|
| WO | WO 2009/126257 | 4/2009 |
| WO | WO 2009/070246 | 6/2009 |
| WO | WO 2010/126459 | 11/2010 |

* cited by examiner

*Primary Examiner* — Daniel S Larkin
*Assistant Examiner* — Jamar Ray
(74) *Attorney, Agent, or Firm* — Foster Pepper PLLC; P. G. Scott Born (57) ABSTRACT A microfluidic device and method of its use. A workable microfluidic device (100) includes a channel (116) extending between an entry aperture (230) and a vent (118). Part of the channel (116) is arranged to permit interrogation of particles carried by a fluid passing therethrough. Suction structure carried on the device (100) is disposed in fluid communication with the channel operably to apply a reduced pressure at the entry aperture (230) effective to infuse an amount of fluid through the entry aperture and into a receiving zone (122, 122', 122") of the channel. The entry aperture (230) is placed into a bulk fluid, and the suction structure is operated to load a sample into the microfluidic device (100).

10 Claims, 8 Drawing Sheets

SAMPLE-ACQUIRING MICROFLUIDIC TESTER

TECHNICAL FIELD

This invention relates to microfluidic devices for detecting, quantifying, qualifying, or otherwise sensing, particles carried by a fluid.

BACKGROUND

Certain microfluidic devices are commercially available. Such devices may be used to interrogate particles carried in a fluid diluent. Exemplary particle interrogation may be electrically-based, optically-based, or both. One effective electrically-based interrogation encompasses particle analysis evidenced by the Coulter effect. An operable optically-based interrogation encompasses detection of fluorescence conventionally known as a Stokes' shift.

Operable microfluidic devices are conventionally arranged to accept a fluid sample that generally encompasses a subset of a bulk fluid. One desirable interrogated sample size for interrogation of whole blood is about 50 µl. An operable arrangement entails loading a 75 µl super-sample into a microfluidic interrogation cassette, of which only 50 µl is typically interrogated. The extra 25 µl may be used to ensure operational readiness of the cassette. Sometimes, essentially the entire super-sample may be interrogated.

A super-sample may be extracted from bulk fluid using a pipetter, syringe, or other fluid transfer device, that can accurately dispense a small quantity of fluid into a receiving well, or entry aperture, in a microfluidic interrogation device. Conceptually, a vent may permit escape of air from the microfluidic interrogation device as the super-sample is injected into the device. In certain cases, surface tension forces may be sufficient to draw the super-sample into a receiving area of the channel. In other cases, a vacuum may sometimes be applied from an external source to the vent to reduce the pressure in a channel passing through the microfluidic device to assist in loading a fluid super-sample into a receiving portion of the channel. In any case, a vacuum is conventionally applied to cause an interrogated-sample portion of fluid to flow through the microfluidic device while performing particle analysis.

DISCLOSURE OF THE INVENTION

The present invention provides an apparatus and method for detecting, quantifying, qualifying, or otherwise sensing, particles carried by a fluid. An exemplary apparatus may be characterized as a microfluidic interrogation device, or cassette. One such interrogation device includes a channel configured and arranged to permit fluid flow there-through. The channel may include a plurality of sub-channel portions that cooperatively form a flow path. Such flow path may be 2-dimensional, or 3-dimensional, in space. Generally, a portion of the channel is configured and arranged to permit interrogation of particles carried by a fluid passing there-through. Such device also typically includes an entry aperture communicating through the channel to a vent; and suction structure disposed in fluid communication with the channel and operable to apply a reduced pressure through a portion of the channel to the entry aperture effective to infuse an amount of fluid through the entry aperture and into a receiving zone of the channel.

Certain operable interrogation devices may include electrode structure configured and arranged to permit particle interrogation according to the Colter effect. Other operable interrogation devices may include radiation transmitting structure arranged to permit detection of fluorescence conventionally known as a Stokes' shift. Certain interrogation devices may be structured to permit either, or both, aforementioned interrogation techniques.

A currently preferred interrogation device includes a plurality of stacked thin film layers, a portion of the channel being formed as a void in at least one layer. Desirably, a portion of the channel is configured to urge particles toward substantially single-file travel there-through. One workable structure effective to urge such single-file travel includes an aperture passing through a layer that is disposed between fluid flow portions of a channel.

Operable suction structure for obtaining a fluid sample may be provided in a variety of configurations. One operable suction structure includes a suction bulb. An exemplary suction bulb may be formed in an exterior layer as a transversely off-set area. A transverse off-set may be formed, for example, by heating and embossing a local area of a layer of film to form a transversely resilient bubble. A currently preferred suction structure includes a void space disposed in at least one interior layer and covered by an exterior layer of a microfluidic device structured as a sandwich and including a plurality of stacked layers. An exemplary void space may encompass a chamber formed by complementary stacking of void spaces in a plurality of layers.

The invention may be embodied in a method for loading a fluid sample into a microfluidic interrogation cassette. One such method includes the steps of: a) providing a microfluidic interrogation cassette including a sample entry aperture; b) applying a bias sufficient to displace suction structure carried by the cassette to a pre-suction configuration in preparation to apply a reduced pressure, or suction, at the entry aperture; c) placing the entry aperture into bulk fluid; and d) releasing the bias to load the sample. It should be realized that steps b) and c) can be performed in any order.

A currently preferred microfluidic interrogation cassette includes a channel configured and arranged to permit fluid flow in a direction from an entry aperture toward an air vent. A portion of the channel is generally arranged to permit interrogation of particles carried by a fluid passing there-through. The preferred cassette also carries suction structure disposed in fluid communication with the channel operably to apply a reduced pressure through a portion of the channel to the entry aperture effective to infuse an amount of fluid through the entry aperture and into a receiving/holding zone.

These features, advantages, and alternative aspects of the present invention will be apparent to those skilled in the art from a consideration of the following detailed description taken in combination with the accompanying drawings.

BRIEF DESCRIPTION OF THE DRAWINGS

In the drawings, which illustrate what is currently considered to be the best mode for carrying out the invention.

BEST MODES FOR CARRYING OUT THE INVENTION

Reference will now be made to the drawings in which the various elements of the invention will be given numerical designations and in which the invention will be discussed so as to enable one skilled in the art to make and use the invention. It is to be understood that the following description is only exemplary of the principles of the present invention, and should not be viewed as narrowing the claims which follow.

Figure 1:
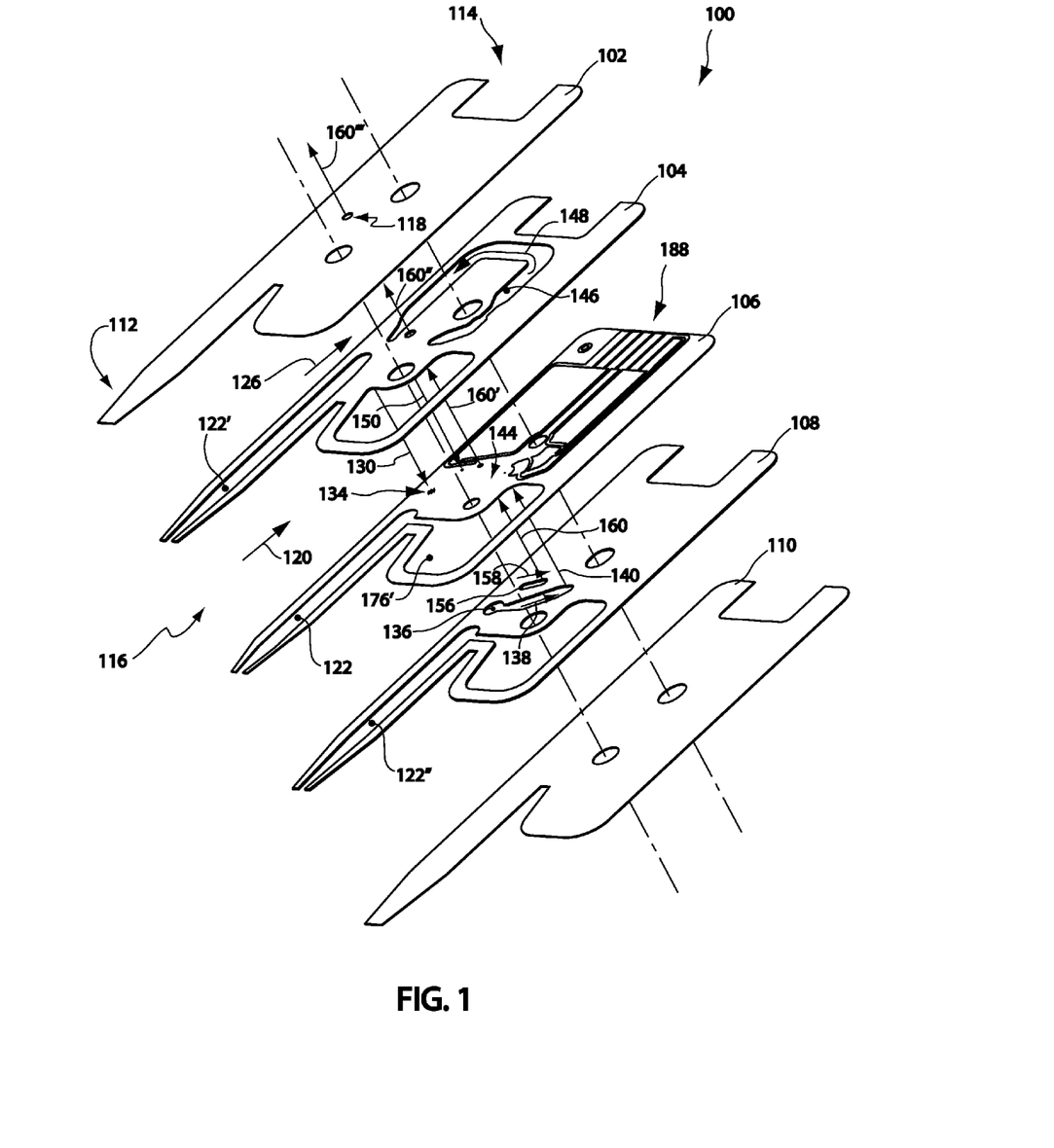
FIG. 1 is an exploded assembly view in perspective from above of a currently preferred embodiment structured according to certain principles of the invention.
Figure 2:
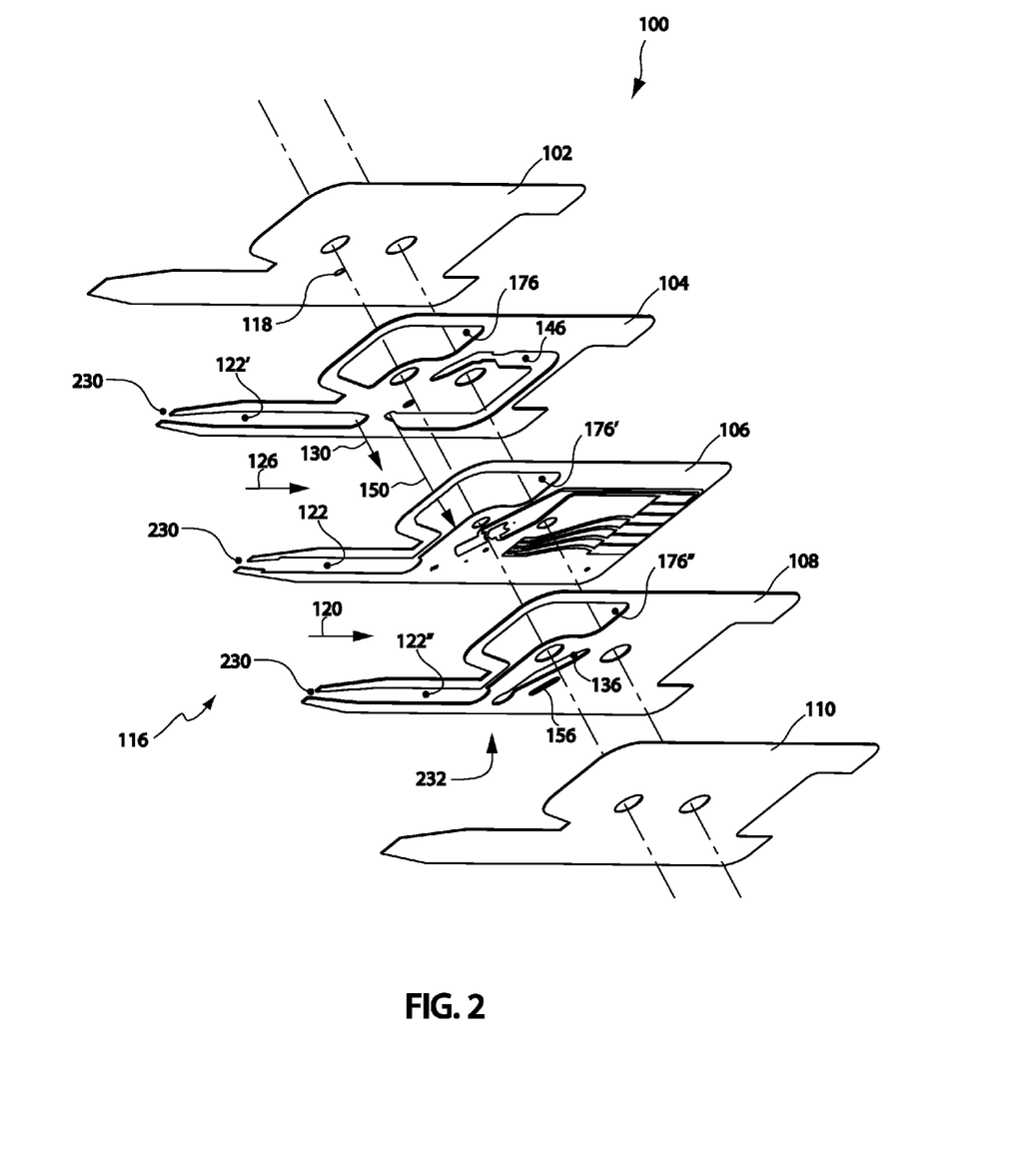
FIG. 2 is an exploded assembly view in perspective from below of the assembly illustrated in FIG. 1.

An exemplary microfluidic interrogation cassette that is structured to permit interrogation of a particle-carrying fluid sample, such as whole blood, is indicated generally at 100 in FIGS. 1 and 2. The illustrated cassette 100 includes a plurality of thin film layers that are bonded together to provide a fluid flow path along cooperating channel portions. Top cap layer 102 is bonded to channel layer 104, which is also bonded to interrogation layer 106. Opposite sides of channel layer 108 are bonded to interrogation layer 106 and bottom cap layer 110, respectively.

Materials of construction of a microfluidic interrogation cassette, such as cassette 100, may be selected from a range of suitable materials that are sized and arranged to perform desired functions. Typically, the thickness of at least the channel and interrogation layers is typically sized in general agreement with a characteristic size of the particles of interest. Alternative configurations to the illustrated example are within contemplation. For example, a cap layer could be replaced by a thicker substrate to provide a more substantial foundation. A substantial foundation may improve ruggedness, and facilitate handling. Such foundation could be formed from alternative materials, e.g. injection molded. An operable cassette may include more, or fewer, layers. Cassettes that do not optically interrogate particles may have thicker (even much thicker) channel layers, because particles which would be disposed to block Stokes' shift radiation near an interrogation aperture do not significantly compromise the Coulter effect.

The illustrated cap layers 102, 110 are formed from transparent polyester film having a thickness of about 0.005 inches (0.127 mm). An operable interrogation layer 106 may be made from an assortment of materials, depending upon the intended use for the particular sensor that will be constructed. A clear polyester film may be used as an interrogation layer in sensors (cassettes) structured to interrogate particles when using only impedance measurements. It is preferred to employ an opaque polyamide film as the interrogation layer in sensors structured to interrogate particles when using both impedance and fluorescence (or even when using only fluorescence). A suitable opaque film inherently resists transmission of undesired radiation toward a Stokes' shift radiation detection sensor. Illustrated interrogation layer 106 is formed from opaque polyamide film having a thickness of about 0.005 inches (0.127 mm). The illustrated channel layers 104, 108 are formed from double-sided adhesive film. A workable such film includes a polyester center carrier layer that is 0.007 inches (0.178 mm) in thickness with a layer of acrylic-based adhesive 0.0015 inches (0.038 mm) in thickness coated onto each side.

The illustrated cassette 100 is structured and arranged to permit manipulation of the cassette 100 using a human hand when loading a sample of fluid and placing the loaded cassette 100 into an interrogation device. A representative cassette 100 extends about 3.5 inches (89 mm) between its distal end, generally 112, and proximal end 114. A representative width of cassette 100 is about 1.2 inches (30.5 mm). Typically, an interrogation device couples to a cassette and provides a fluid motive source (e.g. vacuum) to cause flow of fluid through the cassette, as well as instrumentation effective to interrogate particles carried in the fluid. Exemplary instrumentation may be electrically- or optically-based.

Cassette 100 provides a fluid flow channel, generally 116, extending from distal end 112 toward an air vent aperture, generally 118. Channel 116 includes an interlinked series of cooperating sub-channel portions that, together, extend in 3-dimensional space to form a fluid path through the cassette 100. With particular reference to FIG. 1, and as indicated by fluid-flow arrow 120, a super-sample of fluid can first be inspired from distal end 112 into a holding chamber 122 that is formed as a channel or void space in layer 106. As illustrated, holding chamber 122 may be augmented in volume by combination of one or more cooperating channel or void space in another layer, such as 122' and/or 122". Fluid from the channel 122" then can be drawn through the cassette 100 and toward venting aperture 118, as indicated in-part by fluid-flow arrow 126, to interrogate a desired volume of fluid.

Near the proximal end of channel 122', fluid under influence of a pressure differential (e.g. imposed by an interrogation device, not illustrated) may flow in the through-the-thickness direction, as indicated by fluid-flow arrow 130, passing through an optional debris filter 134 and into channel 136, which is carried in channel layer 108. The fluid flow direction along channel 136 is indicated by fluid-flow arrow 138. Fluid continues in the through-the-thickness direction, as indicated by fluid-flow arrow 140, passing through interrogation aperture 144 and into channel 146 carried in channel layer 104. Fluid then flows along channel 146 as indicated by fluid-flow arrow 148.

Near the end of channel 146, fluid again flows in the through-the-thickness direction, as indicated by fluid-flow arrow 150, passing through interrogation layer 106 and into channel 156 carried in channel layer 108. The fluid flow direction in channel 156 is indicated by fluid-flow arrow 158. Fluid then again flows in the through-the-thickness direction, as indicated by fluid-flow arrows 160, 160', 160" and 160''', potentially passing through all of interrogation layer 106, channel layer 104, and top cap layer 102, before exiting cassette 100 through air vent 118. It is preferred, however, to provide trigger structure operable to terminate fluid flow along channel 116 prior to escape of fluid through air vent 118.

Figure 3:
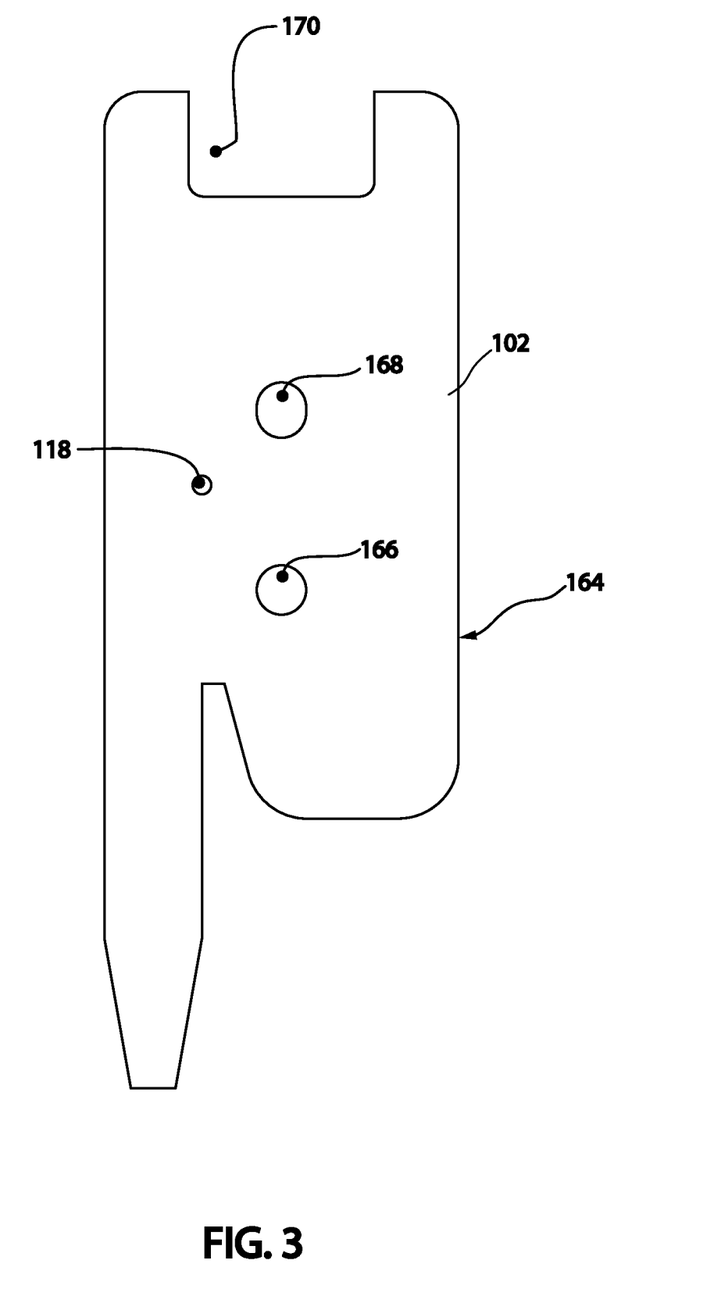
FIG. 3 is a plan view from above of layer 102 of the device 100 illustrated in FIG. 1.

With reference now to FIG. 3, the illustrated cap layer 102 forms a continuous membrane bounded by a perimeter 164 and interrupted only by air vent aperture 118, distal alignment aperture 166, and proximal alignment aperture 168. A window 170 may be provided, as illustrated, to facilitate coupling the cassette 100 to an electrical edge connector of an interrogation device. The axially protruding extensions that bracket window 170 reinforce the proximal end of the interrogation layer 106 to resist buckling of that layer.

Figure 4:
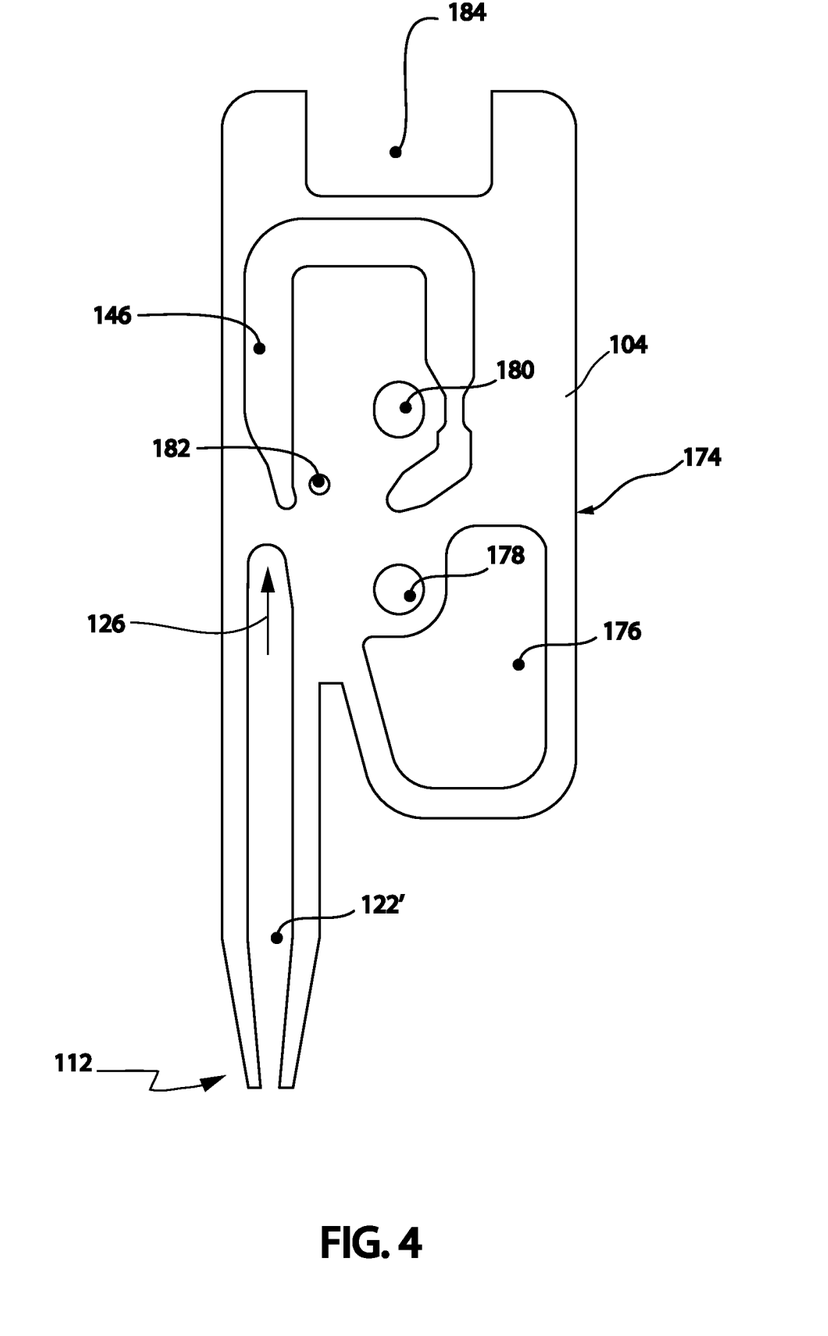
FIG. 4 is a plan view from above of layer 104 of the device 100 illustrated in FIG. 1.

As illustrated in FIG. 4, channel layer 104 has a perimeter 174 that is similar in general outline to that of cap layer 102. However, a through-the-thickness void space in layer 104 is configured to form holding chamber or channel 122' extending proximally from the distal end 112. Other through-the-thickness void spaces in layer 104 form reservoir 176, channel 146, distal alignment aperture 178, proximal alignment aperture 180, and tunnel 182. Channel 146 can be structured to provide a desired interrogated-fluid sample volume between two axially spaced-apart locations. Tunnel 182 permits fluid flow as indicated in FIG. 1 between fluid-flow arrows 160' and 160". A window 184 may be provided to facilitate coupling the cassette 100 to an electrical edge connector of an interrogation device.

Figure 5A:
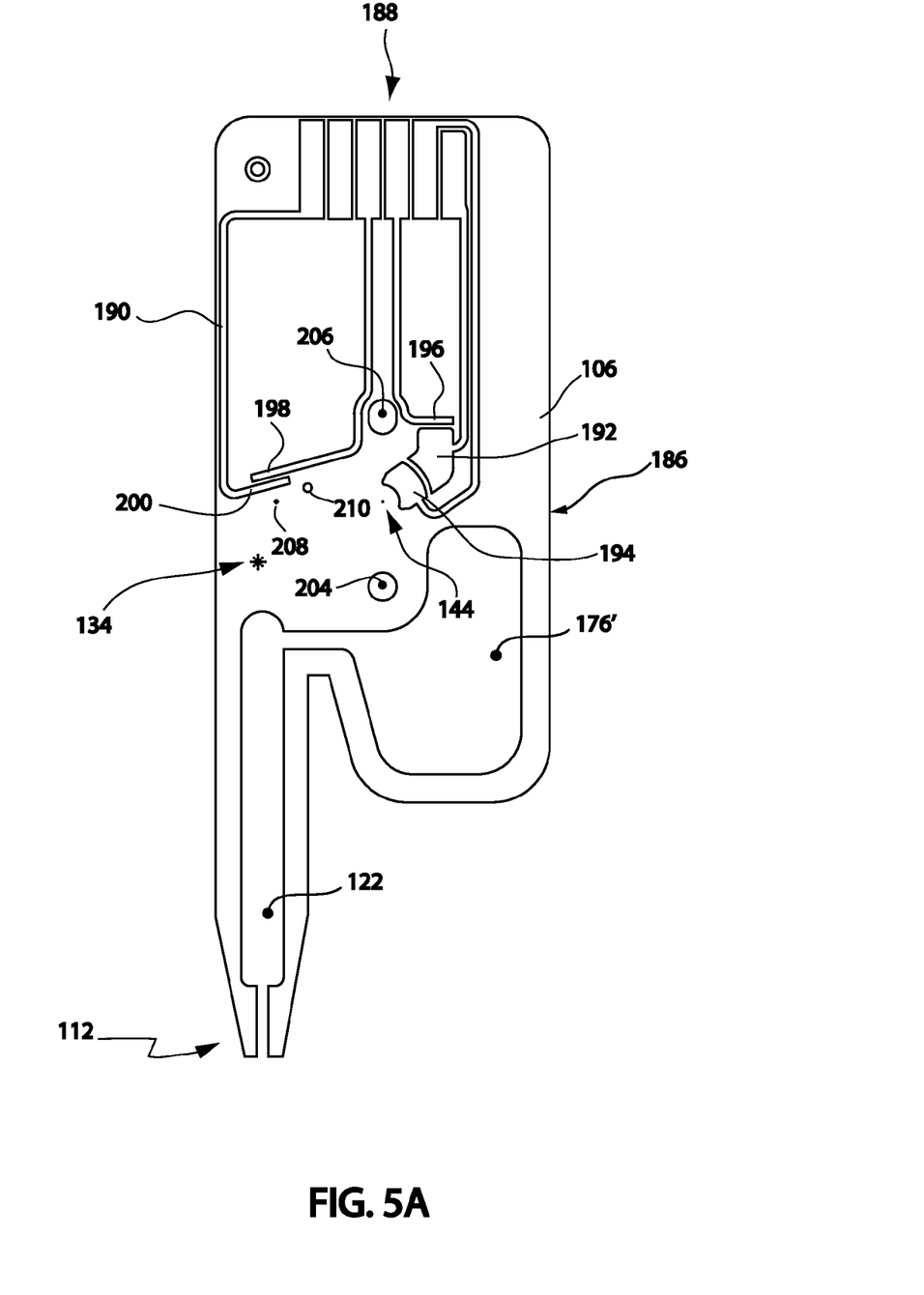
FIG. 5A is a plan view from above of layer 106 of the device 100 illustrated in FIG. 1.
Figure 5B:
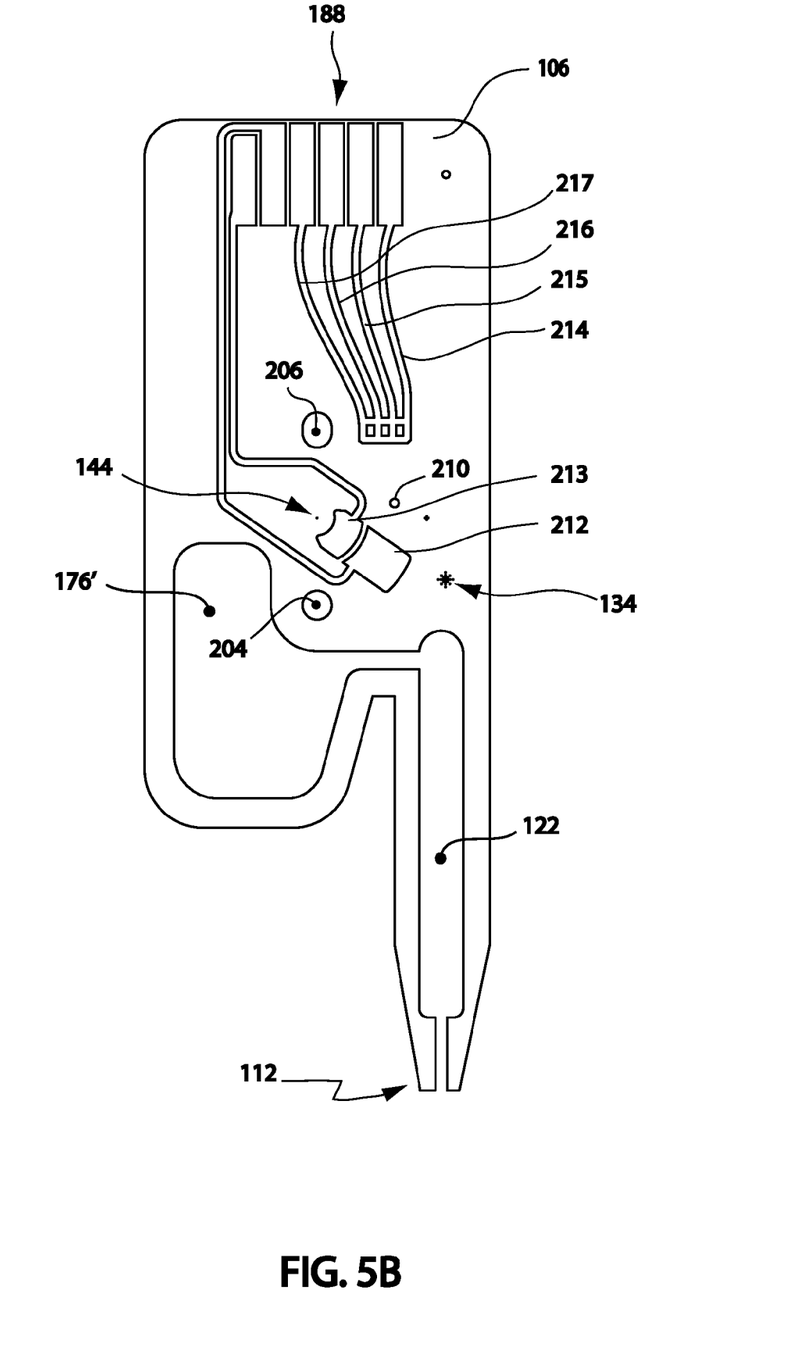
FIG. 5B is a plan view from below of layer 106 illustrated in FIG. 5A.

The exemplary interrogation layer 106 illustrated in FIGS. 5A and 5B has a perimeter 186 that is also similar in general outline to that of cap layer 102. Interrogation layer 106 carries electrically conductive material arranged to provide electrical surface connection pads, generally 188, that communicate through traces (e.g. 190) to electrodes that are disposed at strategic locations. Conventionally, electrode 192 is a driving electrode, and electrode 194 is a measurement electrode. Electrode 196 is positioned for use as an optional start trigger, and is disposed downstream of driving electrode 192 to ensure that all measurement electrodes are properly wet-out by fluid before starting collection of particle data. Fluid coming into contact with electrode 196 is flowing through channel 146 in channel layer 104. Cooperating electrodes 198 and 200 are disposed spaced apart along channel 146 to operate as an optional stop trigger after the desired volume of fluid has been interrogated. A stop trigger can be used to terminate collection of data and also to cease urging fluid flow through channel 116.

Interrogation layer 106 includes through-the-thickness void spaces that form reservoir 176', holding chamber/channel 122, distal alignment aperture 204, proximal alignment aperture 206, interrogation aperture 144, and vias 208 and 210. Via 208 receives fluid indicated by fluid-flow arrow 150, and via 210 passes fluid as indicated by fluid-flow arrow 160' (see FIG. 1).

With reference to FIG. 5B, exemplary electrodes disposed on the bottom of interrogation layer 106 include: driving electrode 212, measurement electrode 213, and electrodes 214-217. Preferably, an alternating electrical signal is applied between the driving electrodes, and impedance is measured between the two measurement electrodes. However, alternative configurations permit operable electrical measurements to detect the Coulter effect. For example, either one of measurement electrodes, 194 and 213, may be used to compare measured impedance with a ground, or other, reference.

Electrode traces 214-217 are configured to enable multiple combinations of conductivity (or non-conductivity) to allow the measurement system the ability to determine which type of cassette has been inserted. Most generally, all four traces (214-217) are manufactured in a state of connectivity between all four contact pads. The connecting system would provide a stimulus signal on one of the contact pads and then subsequently measure each of the other three contact pads to determine the state of connectivity on each of the three measured pads. The default state (with all three connected) would be identified as Type A cassette (for example). Other types of cassettes can be fabricated in subsequent laser manufacturing operations by laser cutting or laser ablating sections of the traces (214-217) to disconnect desired contact pads. Multiple cassette types (e.g. having alternatively arranged electrodes, different flow paths, permitting alternative interrogation—such as Stokes shift, etc.), can be produced using this efficient system.

Figure 6:
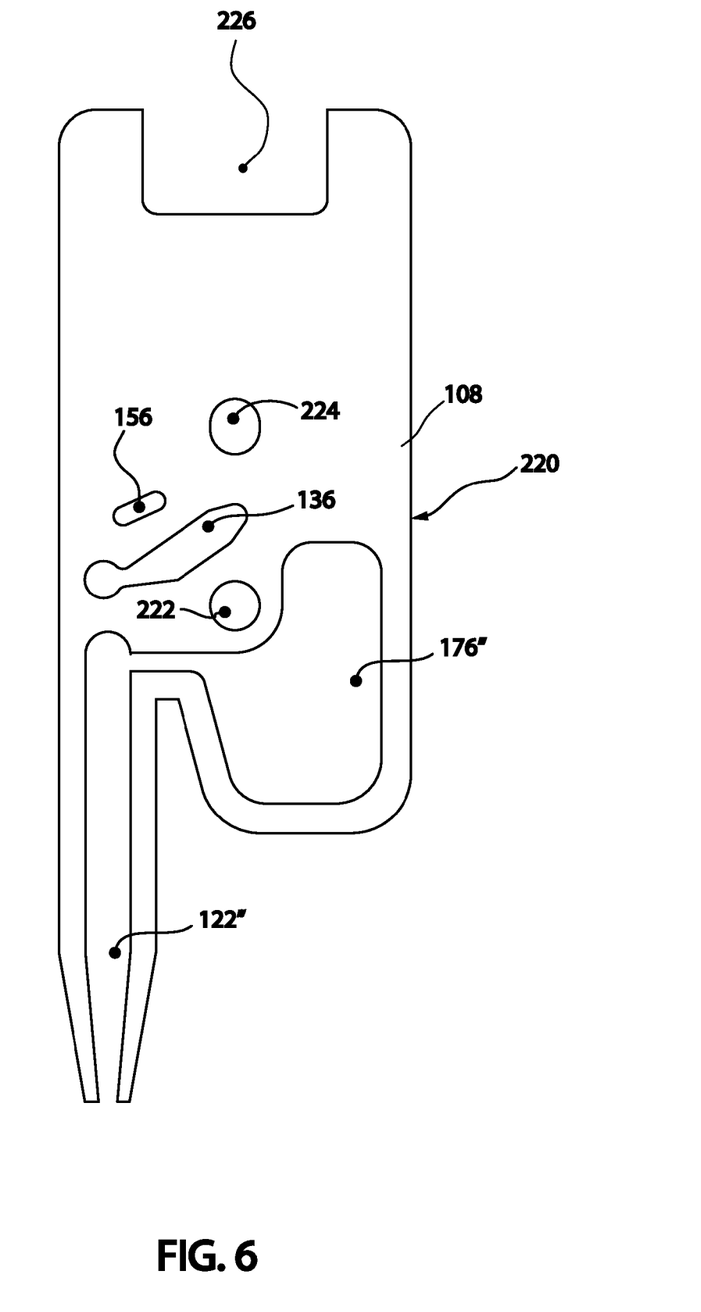
FIG. 6 is a plan view from above of layer 108 of the device 100 illustrated in FIG. 1.

As illustrated in FIG. 6, channel layer 108 has a perimeter 220 that is also similar in general outline to that of cap layer 102. Through-the-thickness void spaces in layer 106 are configured to form: reservoir 176", channel/chamber 122", channel 136, channel 156, distal alignment aperture 222, and proximal alignment aperture 224. A window 226 may be provided to facilitate coupling the cassette 100 to an electrical edge connector of an interrogation device.

Figure 7:
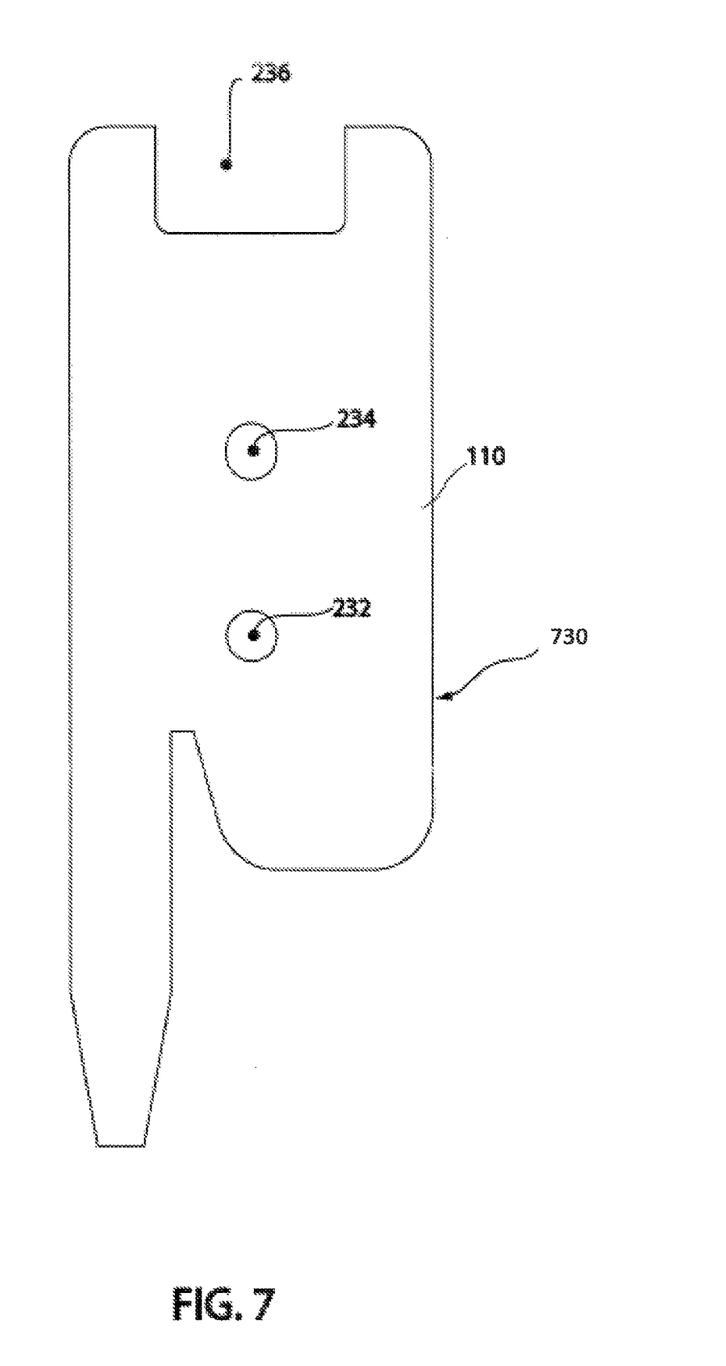
FIG. 7 is a plan view from above of layer 110 of the device 100 illustrated in FIG. 1.

With reference now to FIG. 7, the illustrated cap layer 110 forms a continuous 1 membrane bounded by a perimeter 730 that is similar in general outline to that of cap layer 102 and is interrupted only by distal alignment aperture 232, and proximal alignment aperture 234. A window 236 may be provided, as illustrated, to facilitate coupling the cassette 100 to an electrical edge connector of an interrogation device.

While portions of certain sensors may be die-cut, or otherwise manufactured, it is currently preferred to use an Excimer laser to form the interrogation aperture 144 and alignment apertures 204 and 206. A DPSS laser is operable to form all of the other channel and aperture structure (filters, vents, channels, etc.). The Excimer laser can cut the currently preferred 55 µm diameter interrogation aperture 144 within ±2 microns. Repeatability of the DPSS laser is more like plus/minus 5 microns.

The alignment apertures 204 and 206 are located (laser cut) with extreme precision relative to the laser drilled interrogation aperture 144. The alignment apertures 204 and 206 are also slightly under-sized compared to the alignment apertures in other layers, to ensure the interrogation layer 106 enforces a repeatable loaded position of the cassette 100 during its installation in a preferred interrogation device. At least the initial alignment of a loaded cassette is caused by pins that seat in apertures 204, 206. Use of the more accurate Excimer laser allows the interrogation aperture 144 to be mechanically aligned from cassette to cassette, to the laser beam of a cooperating docking station of a preferred interrogation device with an accuracy of about 20 µm to 50 µm. Here, "accuracy" means that the center of successive interrogation apertures 144 are repeatably disposed within a certain radius of the theoretical centerline of an interrogation zone provided by a cooperatingly structured interrogation device. Sometimes, an installed position of a cassette may be adjusted using feedback from the photodetector used to determine Stokes' shift. In the latter case, a small diameter (and higher energy) laser may be used as a stimulation radiation source, and the cassette will be operably located between the stimulation source and detection sensor.

Cassette 100 includes suction structure (e.g. a suction chamber) disposed in fluid communication with an entry aperture 230 (see FIG. 2) of channel 116 and operable to apply a reduced pressure through a portion of channel 116 to entry aperture 230 effective to infuse an amount of fluid through entry aperture 230 and into a holding chamber, such as chamber 122 in layer 106. The suction structure, generally 232, in the illustrated embodiment 100 is formed by cooperating complementary voids disposed in stacked layers. The suction structure 232 defined in cassette 100 includes reservoir 176 in layer 104, reservoir 176' in layer 106, and reservoir 176" in layer 108; all such reservoirs being covered by resilient portions of respective cap layers 102 and 110. The area encompassed by each of the reservoirs is in general agreement with the contact area between a typical adult human finger and thumb. Therefore, squeezing the resilient area above and below suction structure 232 between finger and thumb applies a suction-inducing bias sufficient to displace suction structure to a pre-suction configuration in preparation to apply a reduced pressure at entry aperture (orifice) 230.

It has surprisingly been discovered that air vent aperture 118 does not have to be restricted to cause a sufficient quantity of fluid to be inspired when aperture 230 is placed into a bulk fluid, and the suction-inducing bias is released. In the illustrated embodiment 100, the impedance to flow of fluid inspired into aperture 230 over a time increment is sufficiently less than the impedance to air flow through the proximal end of channel 116 (including interrogation aperture 144) over that same time increment to permit inspiration of a desired size super-sample into the holding chamber including holding chamber 122.

Alternative suction structure is within contemplation. For example, one operable suction structure includes a resilient suction bulb, or bubble. An exemplary suction bulb may be formed in an exterior layer as a transversely off-set area. A transverse off-set may be formed, for example, by heating and embossing a local area of a layer of film to essentially form a transversely resilient bubble. An alternative bubble can be provided by a dome formed from rubber (or from some other resilient material) that forms a portion of, or is bonded to, a cap layer, with the interior of the dome being placed into fluid communication with channel 116. In any case, the bubble would be placed into fluid communication with the entry aperture 230, and can then be biased preparatory to inspiring a sample or super-sample into a holding chamber.

While the invention has been described in particular with reference to certain illustrated embodiments, such is not intended to limit the scope of the invention. The present invention may be embodied in other specific forms without departing from its spirit or essential characteristics. For non-limiting examples: alternative alignment structure for assembling a cassette, or locating the cassette in registration with respect to an interrogation device, can include a portion of the perimeter of one or more constituent layer; electrodes of any number may be included, and disposed at desired locations, to perform desired functions; certain structures are optional, and in some cases, additional structures may be included in alternative embodiments. Therefore, the described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
   an interrogation device including a channel configured to permit fluid flow through the interrogation device and configured to electronically interrogate particles carried by a fluid passing through the channel;
   an entry aperture in fluid communication with the channel; and
   a pair of flexible cap layers coupled to the interrogation device and between which the interrogation device is disposed, whereby when force is applied urging one cap layer toward the other and the force is subsequently removed, the cap layers, apply a reduced pressure to said entry aperture effective to infuse an amount of the fluid through said entry aperture and into the interrogation device.

2. The apparatus according to claim 1, wherein:
   said interrogation device comprises electrode structure configured and arranged to permit particle interrogation according to the Coulter effect.

3. The apparatus according to claim 2, wherein:
   said interrogation device further comprises structure arranged to permit detection of fluorescence conventionally known as a Stokes' shift.

4. The apparatus according to claim 1, wherein:
   said interrogation device comprises radiation transmitting structure arranged to permit detection of fluorescence conventionally known as a Stokes' shift.

5. The apparatus according to claim 1, wherein:
   said interrogation device comprises a plurality of stacked thin film layers, a portion of said channel being formed as a void caused by at least one layer.

6. The apparatus according to claim 5, wherein:
   said suction structure comprises a void space disposed in at least one interior layer and covered by an exterior layer.

7. The apparatus according to claim 5, wherein:
   said suction structure comprises a suction bulb.

8. The apparatus according to claim 5, wherein:
   said suction bulb is formed in an exterior layer as a transversely off-set area.

9. The apparatus according to claim 1, wherein:
   the cap layers define a reservoir at an end of the channel distal from the ent aperture.

10. The apparatus according to claim 1, wherein:
    a portion of said channel is configured to urge particles toward substantially single-file travel there-through.

\* \* \* \* \*